(12) United States Patent
Bourne et al.

(10) Patent No.: US 7,780,660 B2
(45) Date of Patent: *Aug. 24, 2010

(54) ARTICULATING RADIO FREQUENCY PROBE HANDLE

(75) Inventors: George Bourne, Southborough, MA (US); Robert Rioux, Ashland, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1042 days.

This patent is subject to a terminal disclaimer.

(21) Appl. No.: 11/456,829

(22) Filed: Jul. 11, 2006

(65) Prior Publication Data

US 2006/0247620 A1 Nov. 2, 2006

Related U.S. Application Data

(63) Continuation of application No. 10/345,669, filed on Jan. 15, 2003, now Pat. No. 7,087,051.

(51) Int. Cl.
*A61B 18/18* (2006.01)
(52) U.S. Cl. .......................................... 606/41; 606/46
(58) Field of Classification Search .................. 606/41, 606/45–52, 205–208
See application file for complete search history.

(56) References Cited

U.S. PATENT DOCUMENTS

| 4,483,562 | A | | 11/1984 | Schoolman |
| 5,209,747 | A | * | 5/1993 | Knoepfler .................... 606/16 |
| 5,282,800 | A | | 2/1994 | Foshee et al. |
| 5,395,369 | A | | 3/1995 | McBrayer et al. |
| 5,397,304 | A | | 3/1995 | Truckai |
| 5,458,598 | A | * | 10/1995 | Feinberg et al. ................ 606/52 |
| 5,480,409 | A | | 1/1996 | Riza |
| 5,513,827 | A | | 5/1996 | Michelson |
| 5,527,313 | A | * | 6/1996 | Scott et al. ..................... 606/51 |
| 5,665,085 | A | * | 9/1997 | Nardella ....................... 606/41 |
| 5,849,011 | A | | 12/1998 | Jones et al. |
| 5,861,024 | A | | 1/1999 | Rashidi |
| 6,009,877 | A | | 1/2000 | Edwards |
| 6,030,384 | A | | 2/2000 | Nezhat |
| 6,066,138 | A | | 5/2000 | Sheffer et al. |
| 6,077,286 | A | | 6/2000 | Cuschieri et al. |
| 6,096,033 | A | * | 8/2000 | Tu et al. ........................ 606/31 |

(Continued)

FOREIGN PATENT DOCUMENTS

WO    WO 97/00649 A1    1/1997

*Primary Examiner*—Michael Peffley
(74) *Attorney, Agent, or Firm*—Vista IP Law Group LLP

(57) ABSTRACT

A medical probe assembly and method for ablating tissue using radio frequency energy. The medical probe assembly includes an elongated shaft, a needle electrode array, and a hinged handle. The handle has a collar, which when in the up position covers the hinge so that the device can be used as a conventional medical probe. When the collar is in the down position the hinge is exposed, and the handle can be bent to reduce its overall height. With this reduced height the probe can be used while a patient is lying in a CT scanner or an MRI chamber. Therefore, the surgeon can monitor the ablation during the procedure, and thus avoid unnecessary damage to the surrounding healthy tissue on the one hand, and insufficient ablation of the diseased tissue on the other hand. An alternate embodiment uses a flexible handle instead of a hinged one.

20 Claims, 11 Drawing Sheets

U.S. PATENT DOCUMENTS

| | | |
|---|---|---|
| 6,217,509 B1 | 4/2001 | Foley et al. |
| 6,622,731 B2 | 9/2003 | Daniel et al. |
| 6,726,697 B2 | 4/2004 | Nicholas et al. |
| 2002/0045842 A1 | 4/2002 | Van Bladel et al. |

* cited by examiner

ARTICULATING RADIO FREQUENCY PROBE HANDLE

CROSS REFERENCE TO RELATED APPLICATION

This application is a continuation of U.S. application Ser. No. 10/345,669, filed Jan. 15, 2003, now issued as U.S. Pat. No. 7,087,051, the disclosure of which is hereby incorporated by reference.

FIELD OF THE INVENTION

The field of the present invention relates generally to the structure and use of radio frequency (RF), electro-surgical probes for the treatment of tissue disorders such as tumors and lesions, and more particularly, to handle assemblies for electro-surgical probes.

BACKGROUND OF THE INVENTION

Radio frequency (RF) energy can be used to ablate solid tissue, thus inducing localized tissue necrosis. RF energy is particularly useful in this capacity, for inducing necrosis in sub-dermal lesions and tumors such as those found in cancers of the liver, stomach, kidney, lung, bowel, and pancreas. The conventional delivery system for this sort of treatment is an electro-surgical probe, and one benefit to using such a probe is that it is much less invasive than a full surgical procedure to remove the pathology.

One typical medical probe used for tumor or sub-dermal lesion ablation is comprised of a number of wire needle electrodes in an electrode array that is housed in a cannula. The electrodes in the array are extended into the diseased tissue from the distal end of the cannula, and RF energy is introduced into the tissue via the electrodes. The result is that the tissue thus treated is ablated and the tumor or lesion cells die.

Conventional probes are held using a hollow, rigid handle that is attached to the cannula at the cannula's proximal end. The handle contains wiring that connects the electrode array to an external power source, and a mechanism for extending and retracting the array.

During the surgical procedure, it is highly desirable to be able to monitor the progress of the ablation, to avoid unnecessary damage to the surrounding healthy tissue on the one hand, and insufficient ablation of the diseased tissue on the other hand. Since the ablation is occurring internally, unaided observation is not possible. Therefore, any observation must make use of such imaging techniques as ultrasound imaging, computerized axial tomography (CT) scanning, or magnetic resonance imaging (MRI).

Unfortunately, the more popular CT and MRI imaging techniques require that the patient lie inside a relatively small tubular chamber. In such close quarters there is very little maneuvering room to insert and move or adjust the probe. This problem is compounded if the patient is obese, or if the target region for the RF energy is near the surface of the body, such as when the target region is a shallow sub-dermal lesion.

Since conventional probes have rigid and relatively long handles, they are often unsatisfactory for performing an ablation surgery while simultaneously monitoring its progress using CT or MRI imaging techniques. Moreover, given the equipment that must be housed inside the handle, and the fact that the handle must fit comfortably into the surgeon's hand, it is unrealistic to attempt to solve the problem by shortening the handle enough so that it can be used inside the monitoring chamber.

Consequently, there is a significant need for a medical probe assembly that has a handle that can contain all of the necessary equipment, can comfortably fit into the surgeon's hand, and can be used within the close quarters of a CT scanner or an MRI chamber.

SUMMARY OF THE INVENTION

In accordance with a first aspect of the present inventions, a medical probe assembly for ablating tissue is provided. The medical probe assembly comprises an elongated rigid probe having a proximal end and distal end, one or more ablative elements, such as electrodes or laser fibers, mounted on the probe, and a bendable handle assembly mounted to the proximal end of the probe. By way of non-limiting example, the probe can comprise a cannula and an inner probe slideably disposed within the cannula, in which case, the one or more ablation elements can be mounted to the inner probe and the handle assembly can be mounted to the cannula. Although this invention should not necessarily be so limited in its broadest aspects, the handle assembly can be bent to shorten its length, so that the probe can be manipulated in close quarters, such as, for example, the confined spaces of a CT scanner or an MRI chamber. The handle assembly can optionally be configured to be selectively placed in a locked position, so that the handle assembly is substantially rigid, and an unlocked position, so that the handle assembly is substantially bendable.

The handle assembly can be configured to be selectively be configured to bend in a variety of manners, but in one preferred embodiment, the handle assembly is hinged. For example, the handle assembly can comprise first and second handle pieces, and a hinge coupling the first and second handle pieces. In this case, the handle assembly can optionally include a slideable collar that can be selectively located to cover the hinge to place the handle assembly in a locked position, and to uncover the hinge to place the handle assembly in an unlocked position. As another example, the handle assembly can be flexible. For example, the handle assembly can include a flexible handle. In this case, the handle assembly can optionally include a rigid sleeve that can be selectively located to cover the flexible handle to place the handle assembly in a locked position, and to uncover the flexible handle to place the handle assembly in an unlocked position.

In one preferred embodiment the handle assembly comprises an actuator, which may be, for example, a slideable switch coupled to the one or more ablative elements for selectively deploying and retracting them. The slideable switch can be coupled to the one or more ablative elements through, for example, a flexible push-pull rod.

In the case where the one or more ablative elements are electrodes, the handle assembly can further comprise a radio frequency connector, and one or more radio frequency wires electrically coupled between the connector and the one or more electrodes. The radio frequency wires can be slackened in order to allow the handle assembly to bend without exerting stress on the wires. Alternatively, or additionally, a connector piece may be slideably disposed inside the connector in an interference arrangement. The connector piece is attached to the wires and slides distally when the handle is bent, thus reducing stress on the wires.

In accordance with a second aspect of the present inventions, a medical probe assembly for performing a medical procedure is provided. The medical probe assembly comprises an elongated rigid probe having a proximal end and a distal end, an operative element—such as, for example, a diagnostic or therapeutic element—mounted to the distal end of the probe, and a bendable handle assembly mounted to the proximal end of the probe. The handle assembly additionally comprises an actuator that can be manipulated to deploy the operative element. Optionally, the actuator can be manipulated to also retract the operative element. In one preferred embodiment, the actuator takes the form of the previously described slideable switch. The medical probe assembly, including the handle assembly, may have features similar to those hereinbefore described.

In accordance with a third aspect of the present invention, a method of performing a medical procedure on a patient is provided. The method comprises inserting a medical probe, having a handle, into the patient, placing the patient and medical probe into a confined space, and bending the handle of the medical probe, for example, by hinging or flexing the handle. In the preferred method, the medical probe is inserted into the patient and the handle is bent prior to placing the patient and medical probe into the confined space. However, the medical probe can be inserted into the patient and the handle can be bent after placement of the patient and medical probe into the confined space.

Lastly, the method requires operating the medical probe to perform the medical procedure. By way of non-limiting example, the medical procedure can encompass ablating tissue such as a tumor. If the confined space is formed by a computerized axial tomography chamber, the method can further comprise observing the medical procedure using computerized axial tomography. Likewise, if the confined space is formed by a magnetic resonance chamber, the method can further comprise observing the medical procedure using magnetic resonance imaging. Although the present invention should not be necessarily so limited in its broadest aspects, the bending of the handle allows the medical probe to be more easily manipulated in the confined space. If the medical probe has a deployable operative element, the handle may optionally be manipulated to deploy the operative element, even when the handle is bent.

BRIEF DESCRIPTION OF THE DRAWINGS

The drawings illustrate the design and utility of a preferred embodiment of the present invention, in which similar elements are referred to by common reference numerals. In order to better appreciate the advantages and objects of the present invention, reference should be made to the accompanying drawings that illustrate this preferred embodiment. However, the drawings depict only one embodiment of the invention, and should not be taken as limiting its scope. With this caveat, the invention will be described and explained with additional specificity and detail through the use of the accompanying drawings in which.

DETAILED DESCRIPTION OF THE PREFERRED EMBODIMENTS

Figure 1:
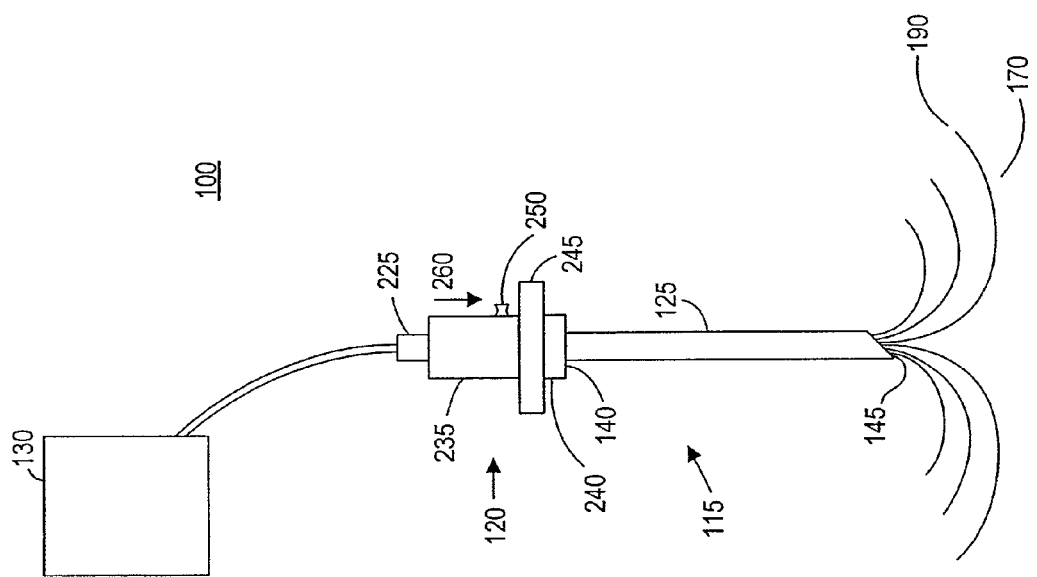
FIG. 1 is a plan view of a tissue ablation system constructed in accordance with one preferred embodiment of the present invention.

FIG. 1 illustrates a tissue ablation system 100 constructed in accordance with a preferred embodiment of the present invention. The tissue ablation system 100 generally comprises an ablation probe assembly 115, which is configured for introduction into the body of a patient to ablate target tissue such as a tumor, and a radio frequency (RF) generator 130 configured for supplying RF energy to the probe assembly 115 in a controlled manner.

Figure 2:
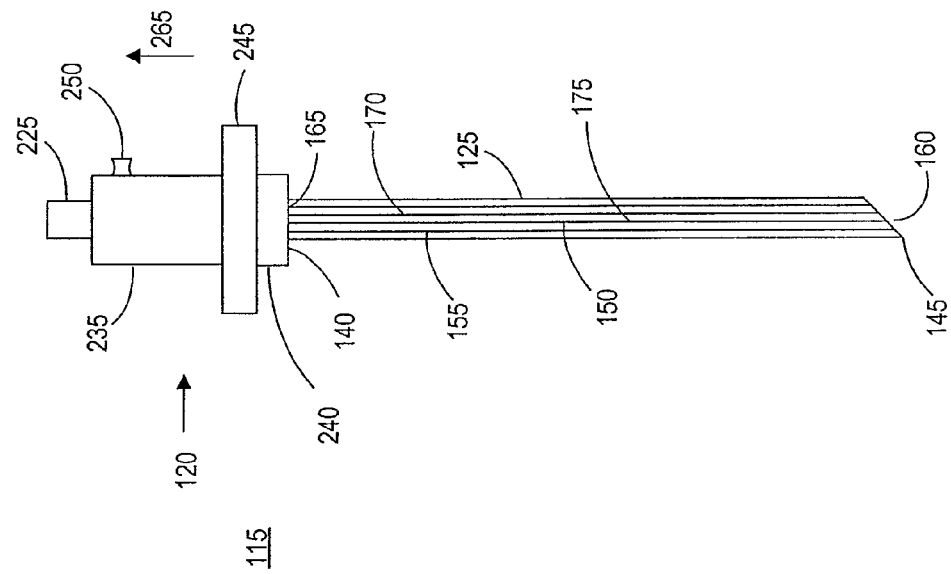
FIG. 2 is a partial cutaway, cross-sectional view of a probe assembly used in the tissue ablation system of FIG. 1, wherein the needle electrode array is particularly shown retracted within the probe assembly.
Figure 3:
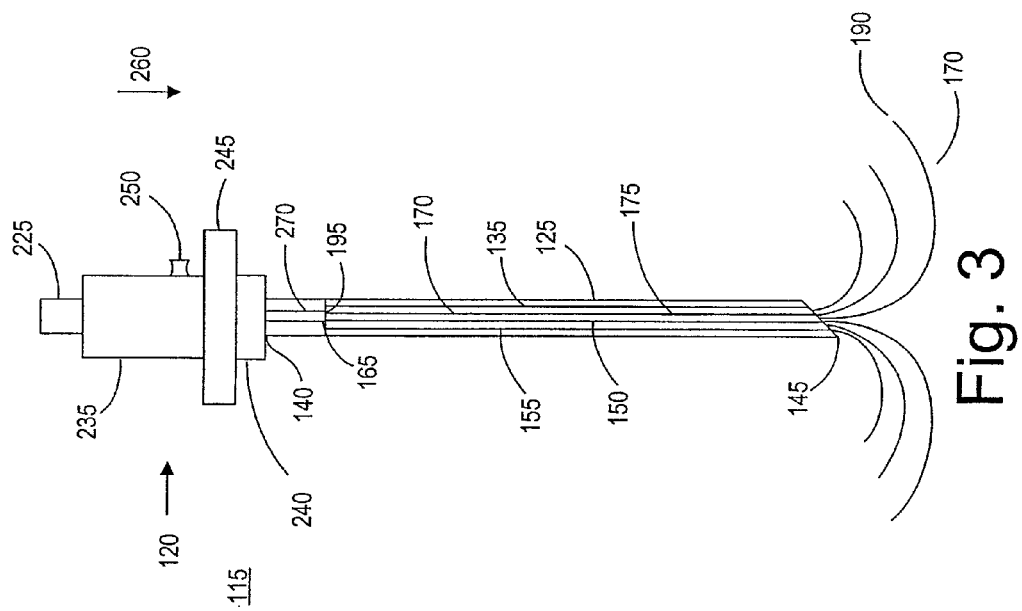
FIG. 3 is a partial cutaway, cross-sectional view of the probe assembly of FIG. 2, wherein the needle electrode array is particularly shown deployed from the probe assembly.

Referring specifically to FIGS. 2 and 3, the probe assembly 115 generally comprises a handle assembly 120, an elongated cannula 125, and an inner probe 135 slideably disposed within the cannula 125. The handle assembly 120 is mounted to the cannula 125 and includes a generator connector 225 that can be electrically coupled to the RF generator 130. As will be described in further detail below, the cannula 125 serves to deliver the active portion of the inner probe 135 to the target tissue. The cannula 125 has a proximal end 140, a distal end 145, and a central lumen 150 extending through the cannula 125 between the proximal end 140 and the distal end 145. The cannula 125 may be rigid, semi-rigid, or flexible depending upon the designed means for introducing the cannula 125 to the target tissue. The cannula 125 is composed of a suitable material, such as plastic or metal, and has a suitable length, typically in the range of 5 cm to 30 cm, preferably from 10 cm to 20 cm. The cannula 125 has an outside diameter consistent with its intended use, typically being from 1 mm to 5 mm, usually from 1.3 mm to 4 mm. The cannula 125 has an inner diameter in the range of 0.7 mm to 4 mm, preferably from 1 mm to 3.5 mm.

The inner probe 135 comprises a reciprocating shaft 155 having a proximal end 165 and a distal end 160, and an array 175 of tissue penetrating needle electrodes 170 extending from the distal end 160 of the shaft 155. Like the cannula 125, the shaft 155 is composed of a suitable material, such as plastic or metal. The electrode array 175 can be mounted anywhere on the shaft 155. However, the electrodes 170 will typically be fastened to the shaft 155 at the shaft's distal end 160, though the individual electrodes 170 can extend up to the shaft's proximal end 165. Each of the needle electrodes 170 is a small diameter metal element, which can penetrate into tissue as it is advanced into a target site within the target region.

As illustrated in FIG. 2, longitudinal translation of the shaft 155 in the proximal direction 265 relative to the cannula 125, retracts the electrode array 175 into the distal end 145 of the cannula 125. When retracted within the cannula 125, the electrode array 175 is placed in a radially collapsed configuration, and each needle electrode 170 is constrained and held in a generally axially aligned position within the cannula 125 to facilitate its introduction into the tissue target site. The probe assembly 115 optionally includes a core member (not shown) mounted on the distal tip 160 of the shaft 155 and disposed within the center of the needle electrode array 175. In this manner, substantially equal circumferential spacing between adjacent needle electrodes 170 is maintained when the array is retracted within the central lumen 150.

As shown in FIG. 3, longitudinal translation of the shaft 155 in the distal direction 260 relative to the cannula 125 deploys the electrode array 175 out of the distal end 145 of the cannula 125. As will be described in further detail, manipulation of the handle assembly 120 will cause the shaft 155 to longitudinally translate to alternately retract and deploy the electrode array 175.

When deployed from the cannula 125, the electrode array 175 is placed in a three-dimensional configuration that usually defines a generally spherical or ellipsoidal volume having a periphery with a maximum radius in the range of 0.5 cm to 4 cm. The needle electrodes 170 are resilient and pre-shaped to assume a desired configuration when advanced into tissue. In the illustrated embodiment, the needle electrodes 170 diverge radially outwardly from the cannula 125 in a uniform pattern, i.e., with the spacing between adjacent needle electrodes 170 diverging in a substantially uniform pattern or symmetric pattern or both. In the illustrated embodiment, the needle electrodes 170 evert proximally, so that they face partially or fully in the proximal direction 265 when fully deployed. In exemplary embodiments, pairs of adjacent needle electrodes 170 can be spaced from each other in similar or identical, repeated patterns that can be symmetrically positioned about an axis of the shaft 155. It will be appreciated by one of ordinary skill in the art that a wide variety of patterns can be used to uniformly cover the region to be treated. It should be noted that a total of six needle electrodes 170 are illustrated in FIGS. 1 and 3. Additional needle electrodes 170 can be added in the spaces between the illustrated electrodes 170, with the maximum number of needle electrodes 170 determined by the electrode width and total circumferential distance available. Thus, the needle electrodes 170 could be quite tightly packed.

Each electrode 170 is preferably composed of a single wire that is formed from resilient conductive metals having a suitable shape memory. Many different metals such as stainless steel, nickel-titanium alloys, nickel-chromium alloys, and spring steel alloys can be used for this purpose. The wires may have circular or non-circular cross-sections, but preferably have rectilinear cross-sections. When constructed in this fashion, the needle electrodes 170 are generally stiffer in the transverse direction and more flexible in the radial direction. The circumferential alignment of the needle electrodes 170 within the cannula 125 can be enhanced by increasing transverse stiffness. Exemplary needle electrodes will have a width in the circumferential direction in the range of 0.2 mm to 0.6 mm, preferably from 0.35 mm to 0.40 mm, and a thickness, in the radial direction, in the range of 0.05 mm to 0.3 mm, preferably from 0.1 mm to 0.2 mm.

The distal ends 190 of the needle electrodes 170 may be honed or sharpened to facilitate their ability to penetrate tissue. The distal ends 190 of these needle electrodes 170 may be hardened using conventional heat treatment or other metallurgical processes. The needle electrodes 170 may be partially covered with insulation, although they will be at least partially free from insulation over their distal portions 190. The proximal ends 195 of the needle electrodes 170 may be directly coupled to the proximal end of the shaft 155, or alternatively, may be indirectly coupled thereto via other intermediate conductors such as RF wires. Optionally, the shaft 155 and any component between the shaft 155 and the needle electrodes 170 are composed of an electrically conductive material, such as stainless steel, and may therefore conveniently serve as intermediate electrical conductors.

In the illustrated embodiment, the RF current is delivered to the electrode array 175 in a mono-polar fashion. Therefore, the current will pass through the electrode array 175 and into the target tissue, thus inducing necrosis in the tissue. To this end the electrode array 175 is configured to concentrate the energy flux in order to have an injurious effect on tissue. However, there is a dispersive electrode (not shown) which is located remotely from the ablation electrode 170, and has a sufficiently large area—typically 130 $cm^2$ for an adult—so that the current density is low and non-injurious to surrounding tissue. In the illustrated embodiment, the dispersive electrode may be attached externally to the patient, using a contact pad placed on the patient's skin. In a mono-polar arrangement, the needle electrodes 170 are bundled together with their proximal portions 195 having only a single layer of insulation over the entire bundle.

Alternatively, the RF current is delivered to the electrode array 175 in a bipolar fashion, which means that current will pass between "positive" and "negative" electrodes 170 within the array 175. In a bipolar arrangement, the positive and negative needle electrodes 170 will be insulated from each other in any regions where they would or could be in contact with each other during the power delivery phase.

Further details regarding needle electrode array-type probe arrangements are disclosed in U.S. Pat. No. 6,379,353, entitled "Apparatus and Method for Treating Tissue with Multiple Electrodes," which is hereby expressly incorporated herein by reference.

The probe assembly 115 may optionally have active cooling functionality, in which case, a heat sink (not shown) can be mounted within the distal end 160 of the shaft 155 in thermal communication with the electrode array 175, and cooling and return lumens (not shown) can extend through the shaft 155 in fluid communication with the heat sink to draw thermal energy away back to the proximal end 165 of the shaft 155. A pump assembly (not shown) can be provided to convey a cooling medium through the cooling lumen to the heat sink, and to pump the heated cooling medium away from the heat sink and back through the return lumen. Further details regarding active cooling of the electrode array 175 are disclosed in co-pending U.S. application Ser. No. 10/387,812, entitled "Passively Cooled Array," which is hereby expressly incorporated herein by reference.

Referring back to FIG. 1, as previously noted, the RF generator 130 is electrically connected, via the generator connector 225, to the handle assembly 120, which is directly or indirectly electrically coupled to the electrode array 175. The RF generator 130 is a conventional RF power supply that operates at a frequency in the range of 200 KHz to 1.25 MHz, with a conventional sinusoidal or non-sinusoidal wave form. Such power supplies are available from many commercial suppliers, such as Valleylab, Aspen, and Bovie. Most general purpose electro-surgical power supplies, however, operate at higher voltages and powers than would normally be necessary or suitable for controlled tissue ablation.

Thus, such power supplies would usually be operated at the lower ends of their voltage and power capabilities. More suitable power supplies will be capable of supplying an ablation current at a relatively low voltage, typically below 150V (peak-to-peak), usually being from 50V to 100V. The power will usually be from 20 W to 200 W, usually having a sine wave form, although other wave forms would also be acceptable. Power supplies capable of operating within these ranges are available from commercial vendors, such as RadioTherapeutics of San Jose, Calif., which markets these power supplies under the trademarks RF2000™ (100 W) and RF3000™ (200 W).

Referring generally to FIGS. 4-8, the handle assembly 120 will now be described. In the preferred embodiment the probe handle assembly 120 is cylindrical. However, it will be obvious to one skilled in the art that the probe handle assembly can be have other shapes as well.

Figure 4:
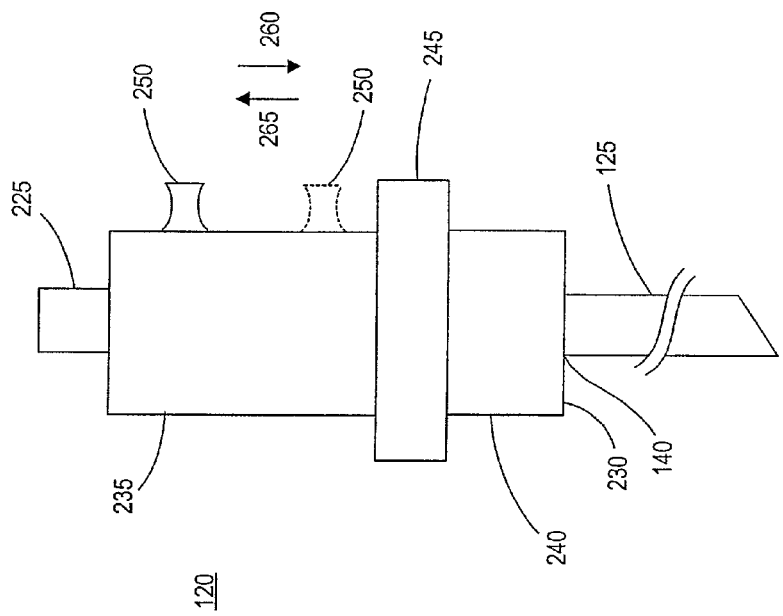
FIG. 4 is a side view of a hinged medical probe handle that can be used in the probe assembly of FIG. 3, wherein the probe handle is particularly shown in a locked unbent position.
Figure 5:
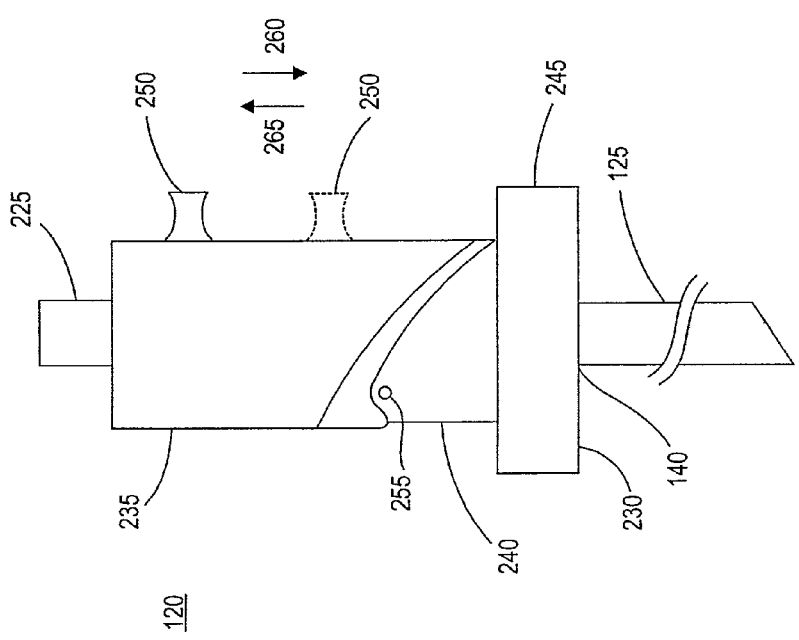
FIG. 5 is a side view of the hinged medical probe handle, wherein the probe handle is particularly shown in an unlocked unbent position.

As illustrated in FIGS. 4 and 5, the probe handle assembly 120 comprises a proximal handle piece 235 and a distal handle piece 240 connected by a hinge 255, a slideable collar 245, and an actuator, such as, for example, a switch 250, that slides relative to the proximal handle piece 235, so that the electrode array 175 can be selectively deployed out from the distal end 145 of the cannula 125 and retracted within the distal end 145 of the cannula 125 in a conventional manner.

Figure 6:
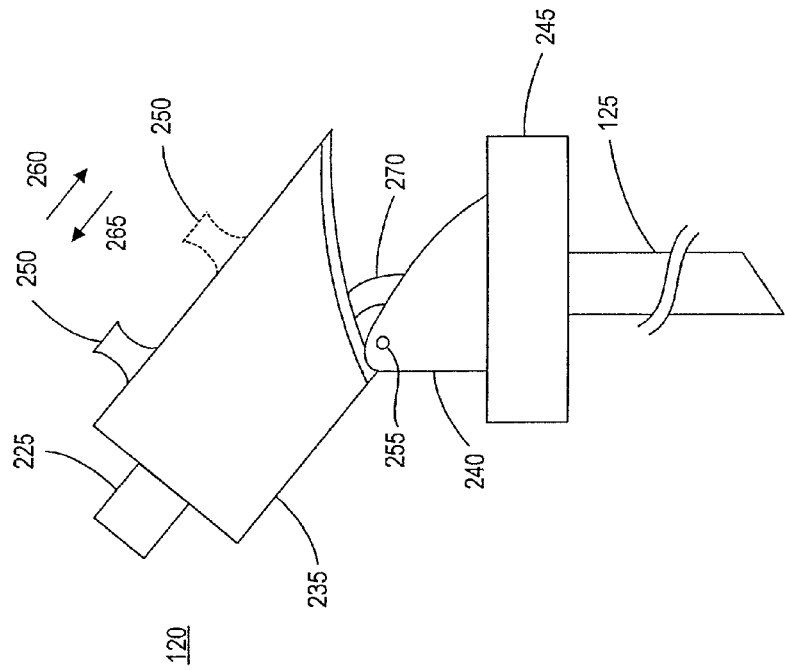
FIG. 6 is a side view of the hinged medical probe handle, wherein the probe handle is particularly shown in an unlocked bent position.

The probe handle assembly 120 is designed so that when the collar 245 is in the up position, as in FIG. 4, i.e., the collar 245 is slid proximally over the hinge 255, the hinge 255 is covered and hence locked. In this manner, the proximal handle piece 235 and the distal handle piece 240 are prevented from rotating relative to each other, thereby allowing the probe handle assembly 120 to be operated as a rigid conventional handle, for use, for example, when the space in which the physician is operating is not confined. The probe handle assembly 120 is also designed so that when the collar 245 is in the down position, as in FIG. 5, i.e., the collar 245 is slid distally past the hinge 255, the hinge 255 is exposed. In this manner, the proximal handle piece 235 and the distal handle piece 240 can rotate relative to each other at the hinge 255, thereby allowing the probe handle assembly 120 to be bent at the hinge 255, as shown in FIG. 6, so that the overall height of the probe handle assembly 120 is reduced. This reduction in height makes it possible to operate the probe assembly 115 within the confines of a CT scanner or an MRI chamber, even if the patient is obese or the target region for treatment is a sub-dermal lesion that is close to the body surface. The result is that ablation can be monitored during treatment, thus ensuring both that the surrounding healthy tissue is not damaged and that all of the target tissue is ablated.

As illustrated in FIG. 5, the hinge 255 is a pin 255 connecting the distal handle piece 240 to the proximal handle piece 235. However, it will be obvious to one skilled in the art that the hinge 255 can be constructed using other hinge designs. The hinge 255 should be located near the distal end 230 of the probe handle assembly 120 where the cannula 125 is attached. More precisely, the hinge 255 should be positioned low enough on the body of the probe handle assembly 120 so that the electrode array 175 can be deployed. In particular, when the collar 245 is in the up position, it remains lower down on the body of the probe handle assembly 120 than the switch 250 is when the switch 250 is in the down position 260. This structure ensures that the collar 245 does not interfere with the operation of the switch 250 regardless of the position of either the switch 250 or the collar 245. An added benefit to locating the hinge 255 near the distal end 230 of the probe handle assembly 120 is that the lower down on the probe handle assembly 120 that the hinge 255 is, the greater the reduction in overall height when the probe handle assembly 120 is bent at the hinge 255.

Figure 7:
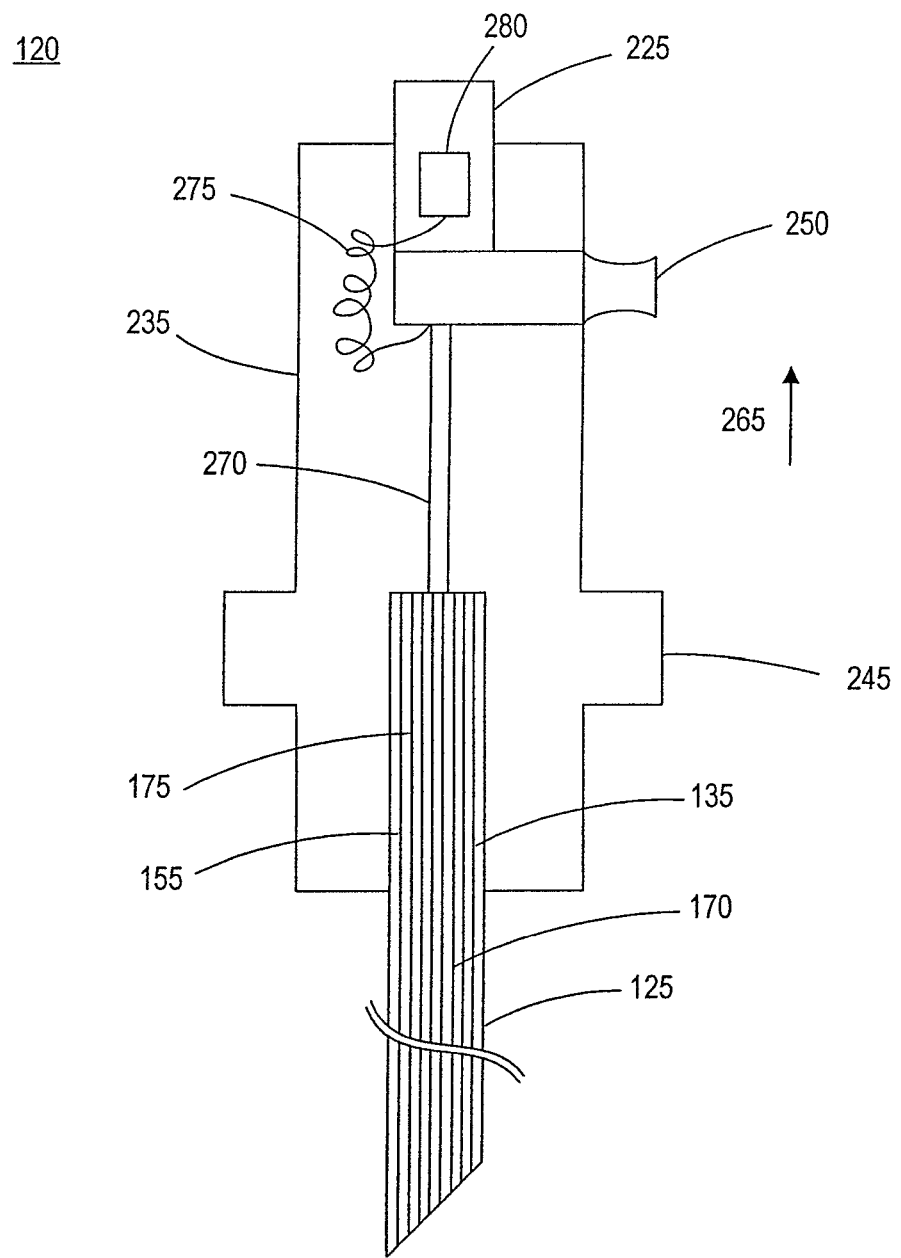
FIG. 7 is a partial cutaway, cross-sectional view of the hinged medical probe handle, wherein the probe handle is particularly shown in the locked unbent position.
Figure 8:
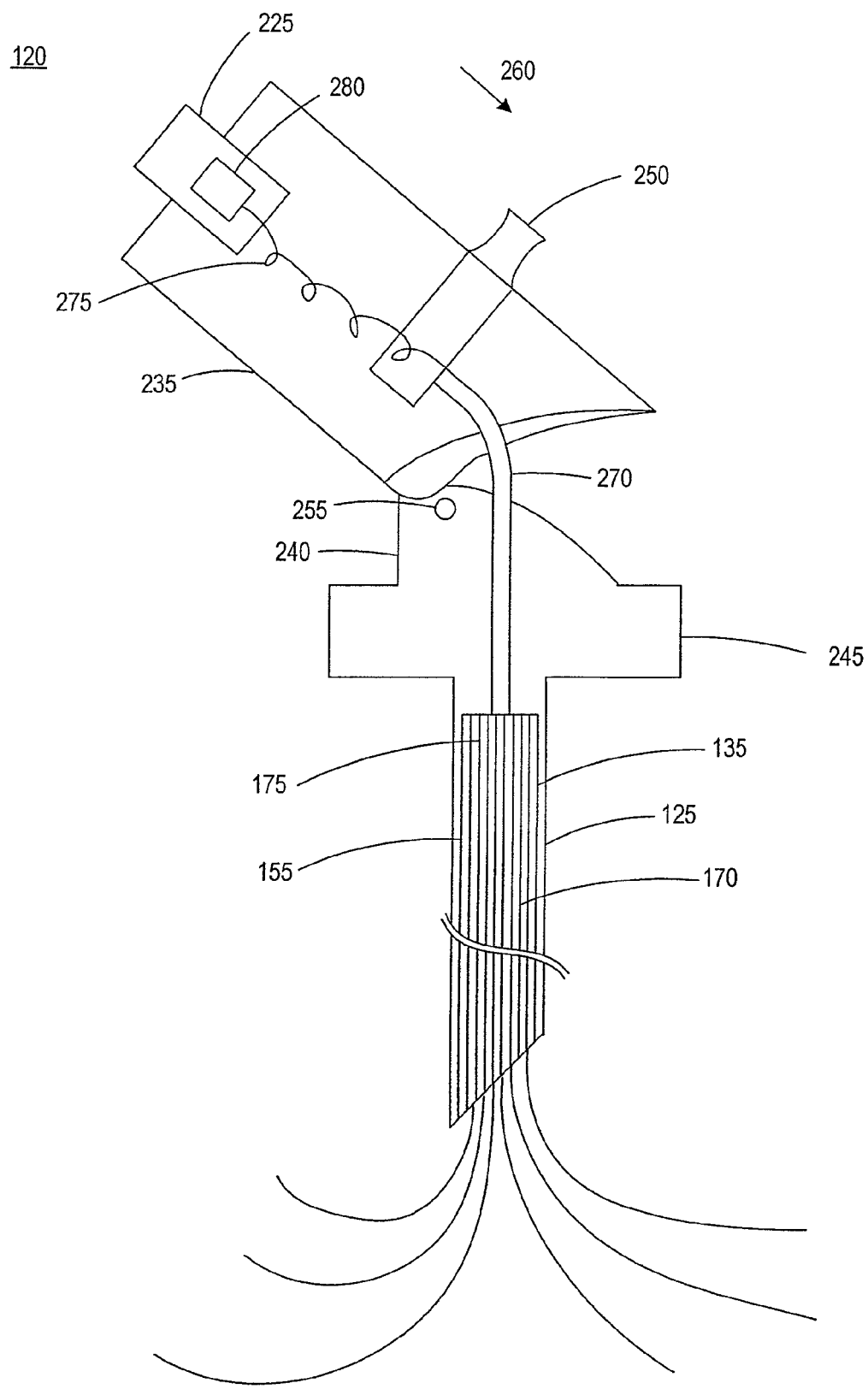
FIG. 8 is a partial cutaway, cross-sectional view of the hinged medical probe handle, wherein the probe handle is particularly shown in the unlocked bent position.

Referring to FIGS. 7 and 8, the probe handle assembly 120 comprises a flexible cable 270 that connects the switch 250 to the shaft 155 of the inner probe 135. The flexible cable 270 has columnar strength, so that it acts as a push-pull rod. Thus, when the switch 250 is pushed into the down position 260, as shown in FIG. 8, it pushes the cable 270, which in turn pushes shaft 155, and thus the distally mounted electrode array 175 into the deployed position. In contrast, when the switch 250 is pushed into the up position 265, as shown in FIG. 7, it pulls the cable 270, which in turn pulls the shaft 155, and thus the electrode array 175 into the retracted position inside the cannula 125. The flexibility of the cable 270 ensures that when the collar 245 is in the down position and the probe handle assembly 120 is bent at its hinge 255, as shown in FIG. 8, the electrode array 175 remains deployed.

As shown in FIGS. 7 and 8, the probe handle assembly 120 also comprises one or more electrical wires 275 that electrically connect the generator connector 225 to the proximal ends of the needle electrode array. The wires 275 may go through or around the switch 250, and through or around the cable 270, depending on whether the switch 250 and cable 270 are hollow. Alternatively, the cable 270 can be conductive, and the wires 275 can connect to the cable 270 at its proximal end. In this alternative the cable 270 conducts power from the wires 275 to the electrodes 170. In the illustrated embodiment, there is one wire 275 which has slack to ensure that when the probe handle assembly 120 is bent there is no stress exerted on the wire 275. Thus, the slack in the wire 275 ensures that there is no loss of power during bending.

Alternatively, or additionally, the generator connector 225 can be hollow and a connector piece 280 can be slideably disposed inside the connector 225 in an interference arrangement. The connector piece 280 is conductive and in conductive contact with the connector 225, and connected to the wire 275. When the handle assembly 120 is bent as in FIG. 8, the connector piece 280 slides distally within the connector 225, thus reducing stress on the wire 275. The slideable connector piece 280 can be used in tandem with slack in the wire 275 to ensure that whether the handle assembly 120 is bent or straight, there is never any stress on the wire 275, and hence there is never a loss of power to the electrode array 175.

Figure 10:
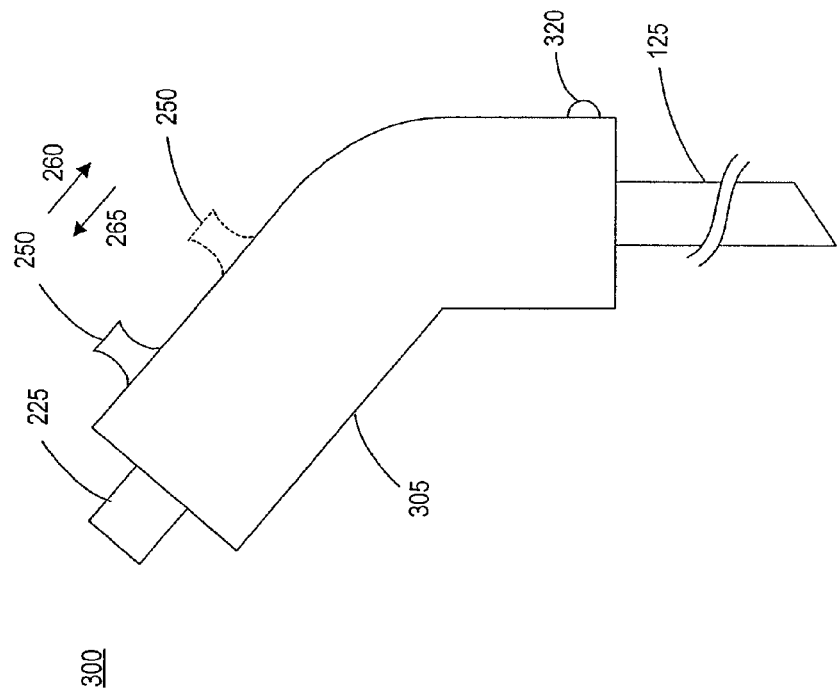
FIG. 10 is a side view of the flexible medical probe handle of FIG. 9, wherein the probe handle is particularly shown in a bent position.
Figure 9:
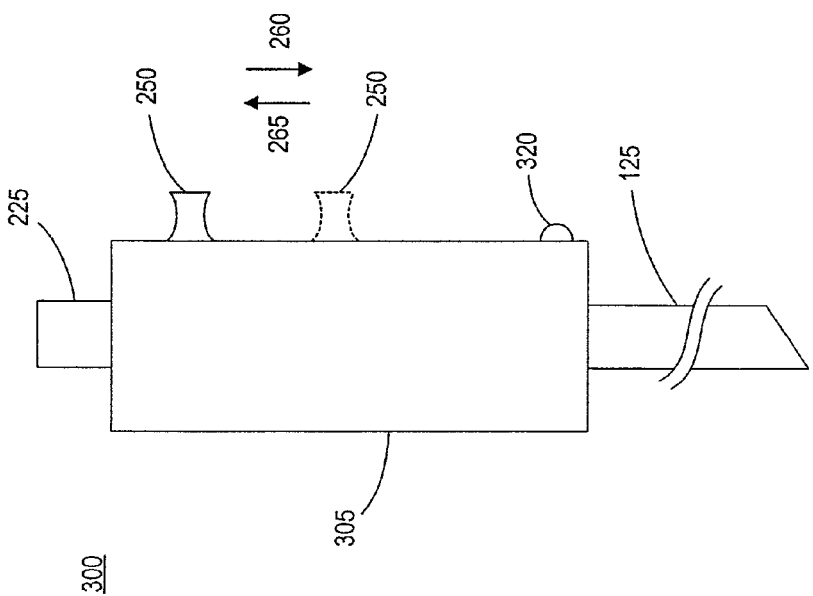
FIG. 9 is a side view of a flexible medical probe handle that can be used in the probe in the probe assembly of FIG. 3, wherein the probe handle is particularly shown in an unbent position.
Figure 11:
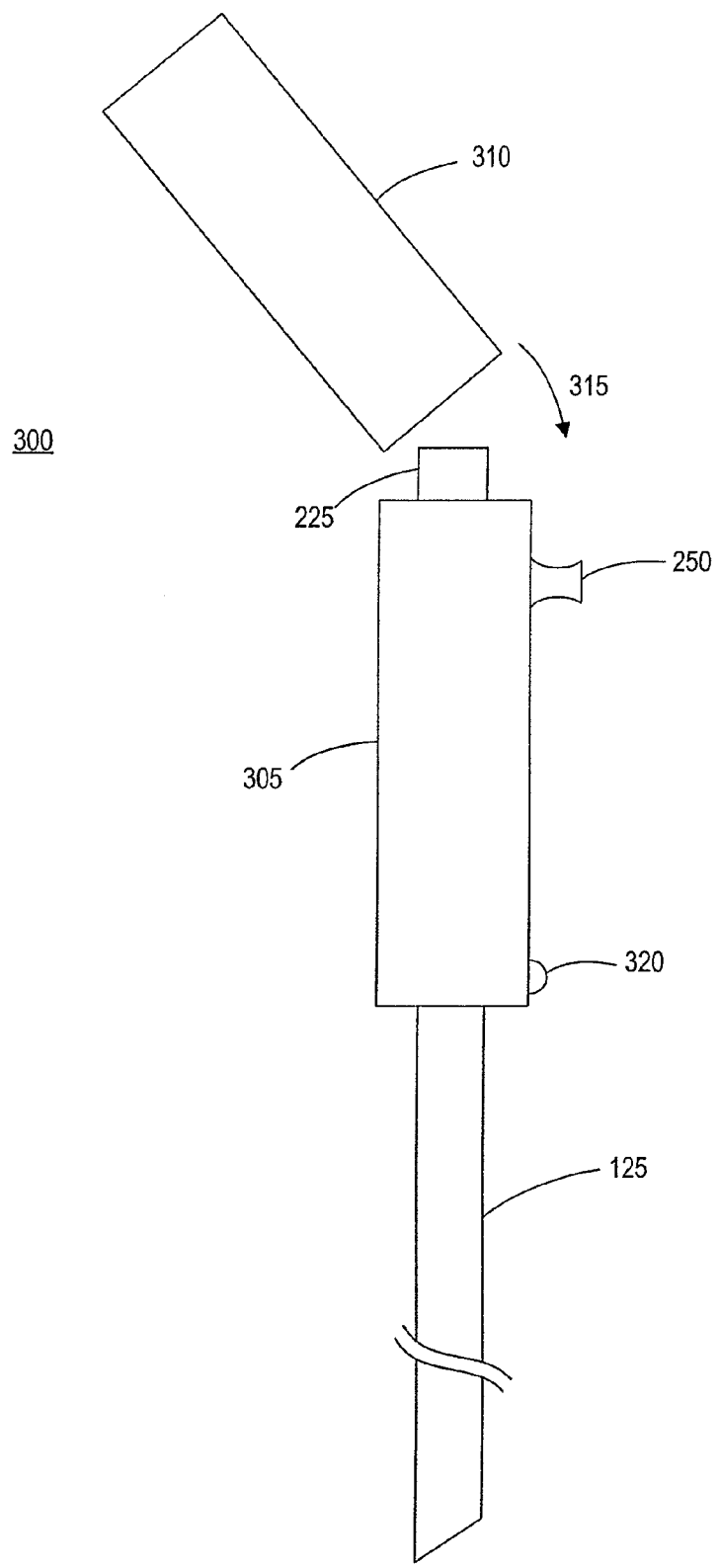
FIG. 11 is a side view of the flexible medical probe handle, particularly showing an optional rigid sleeve.

Referring to FIGS. 9-11, an alternative embodiment of a medical probe assembly 300 that can be used in the tissue ablation system 100 is illustrated. The medical probe assembly 300 is similar to the previously described medical probe assembly 200, with the exception that the medical probe assembly 300 comprises a flexible handle 305 that is mounted to the cannula 125, rather than the hinged handle assembly 120.

Specifically, during operation, the handle 305 can be bent from an upright position (FIG. 9) to a bent position (FIG. 10), so that the probe can be used in the close quarters of a CT scanner or an MRI chamber, again facilitating the continuous monitoring of the ablation process. In the illustrated embodiment, the flexible handle 305 is composed of a low durometer polymer to ensure that once the handle 305 is flexed, it will stay bent until it is straightened by the physician.

The medical probe assembly 300 optionally includes a rigid sleeve 310 that fits over the flexible handle 305, as illustrated in FIG. 11. Preferably, the sleeve 310 has a slot (not shown), so that when the sleeve 310 is placed over the handle 305 the switch 250 conveniently slides into the slot. Thus, when the probe assembly 300 is to be used as a conventional probe assembly 300 with a rigid handle, the sleeve 310 is placed over the flexible handle 305 and locked into place using a conventional locking mechanism.

For example, the sleeve 310 can be locked into place using a "bump and groove" locking mechanism. Specifically, the locking mechanism can include a bump 320 that protrudes from the base of the handle 305, and a groove (not shown) in the inside of the sleeve 310. The sleeve 310 is place over the handle 305 so that the bump 320 fits inside the groove, thus locking the sleeve 310 in place. Alternatively, the bump can be in the interior of the sleeve 310 and the groove on the exterior of the handle 305, so that the roles of the bump and groove are reversed. It will, of course, be obvious to one of ordinary skill in the art, that other locking mechanisms can be employed without departing from the spirit of the present invention. When the probe assembly 300 is to be used in the close quarters of an imaging chamber, the rigid sleeve 310 is removed and the handle 305 is flexed.

The flexible handle 305 comprises many of the same components that the hinged handle assembly 120 has, such as, for example, the switch 250 slideably disposed on the side of the handle 305, and the generator connector 225 for connecting the probe assembly 300 to the RF generator 130. Indeed, the internal workings are essentially identical to the hinged handle assembly 120. The main difference between the hinged handle assembly 120 and the flexible handle assembly 300 is the means by which the handle is bent. With the hinged handle assembly 120, the collar 245 is slid down distally to reveal the hinge 255, and the handle assembly 120 is bent at the hinge 255 to reduce the overall probe assembly 300 height. With the flexible handle 305, the optional sleeve 310 is removed and the handle 305 is flexed to reduce the overall probe assembly 300 height.

Having described the structure of the tissue ablation system 100, its operation 400 in treating targeted tissue will now be described. The treatment may be located anywhere in the body where hyperthermic exposure may be beneficial. Most commonly, the treatment region will comprise a solid tumor within or on an organ of the body such as the liver, kidney, pancreas, breast, and prostate (not accessed via the urethra). The volume to be treated will depend on the size of the tumor or other lesion, typically having a total volume from 1 cm³ to 150 cm³, and often from 2 cm³ to 35 cm³. The peripheral dimensions of the treatment region will sometimes be regular, such as, for example, when they are spherical or ellipsoidal. However, the dimensions will more usually be irregular. The target region may be identified prior to treatment using conventional imaging techniques that are capable of elucidating a target tissue such as a tumor. These imaging techniques include ultrasonic scanning, MRI, CT scanning, fluoroscopy, and nuclear scanning using radio-labeled tumor specific probes.

Referring now to FIGS. 12-15, one preferred method of using the tissue ablation system 100 to perform an ablation procedure on a patient 420 is shown. FIGS. 12-15 illustrate the use of the hinged handle assembly 220, but as will be discussed below, the flexible handle assembly 300 can optionally be used. This procedure is now described.

Figure 12:
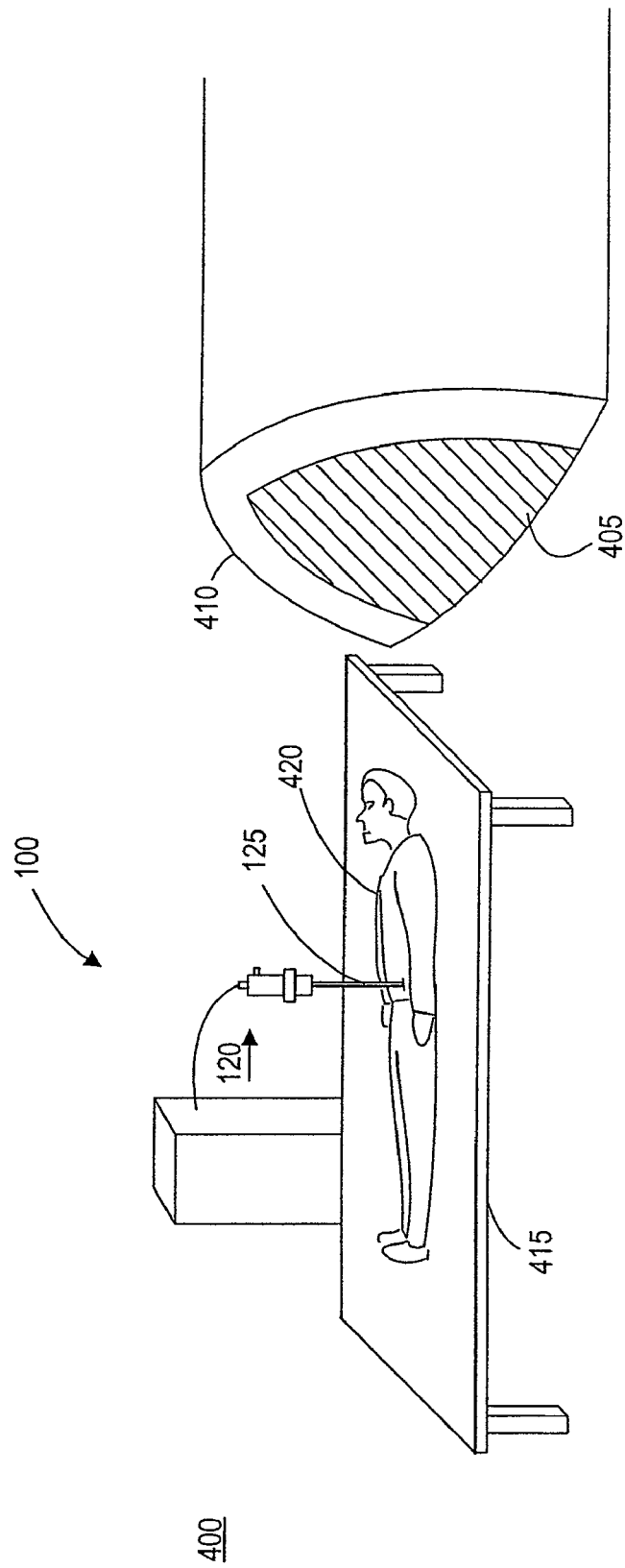
FIG. 12 is a perspective view of a patient being operated on using the tissue ablation system of FIG. 1, wherein the probe assembly of FIG. 2 is particularly shown inserted into the body of the patient in the locked unbent position prior to placement of the patient into an imaging chamber.

The operation of the tissue ablation system 100 is described in treating a treatment region, such as a tumor, within a larger volume of tissue located beneath the skin, or inside or on the surface of an organ of a patient 420. The patient 420 is placed on a patient table 415, and the cannula 125 of the probe assembly 115 is inserted into the patient 420 as shown in FIG. 12. The cannula 125 is first introduced within the treatment region, so that the distal end 145 of the cannula 125 is located at the target site which lies within the treatment region. This can be accomplished using any one of a variety of techniques. For example, the cannula 125 and inner probe 135 may be introduced into the target site percutaneously—i.e., directly through the patient's skin—or through an open surgical incision. When the introduction is done percutaneously, the cannula 125 may have a sharpened tip like a needle, to facilitate introduction into the treatment region. In this case, it is desirable that the cannula 125 be sufficiently rigid, i.e., have a sufficient columnar strength, so that it can be accurately advanced through the larger surrounding volume of tissue.

Alternatively, the cannula 125 may be introduced using an internal stylet that is subsequently exchanged for the shaft 155 and electrode array 175. In this latter case, the cannula 125 can be relatively flexible, since the initial columnar strength will be provided by the stylet.

In yet another alternative approach, a component or element may be provided for introducing the cannula 125 into the target site. For example, a conventional sheath and sharpened stylet assembly can be used to initially access the tissue. The assembly can be positioned using ultrasonic or other conventional imaging, and then the stylet can be removed to leave an access lumen through the sheath. The cannula 125 and inner probe 135 may then be introduced into the tissue surrounding the target tissue through the sheath lumen, so that the distal end 145 of the cannula 125 advances from the sheath into the target site.

Figure 13:
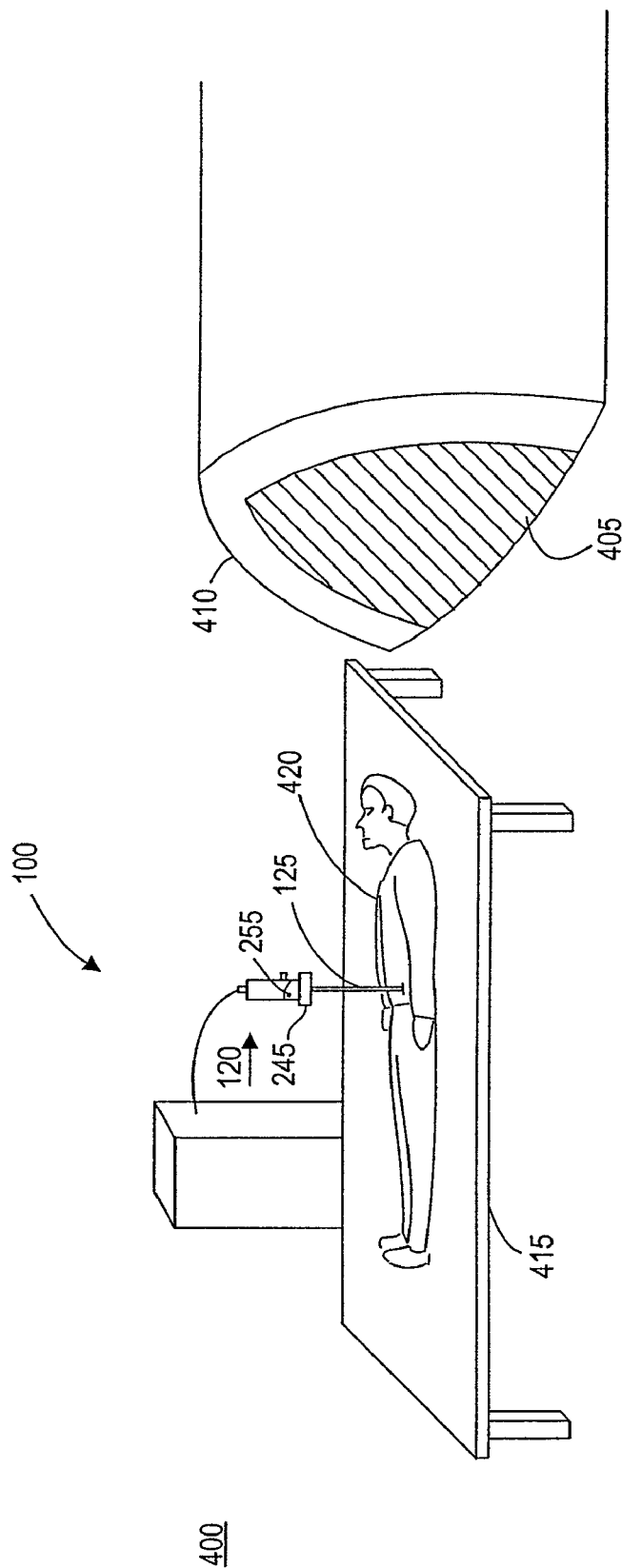
FIG. 13 is a perspective view of the patient, wherein the probe handle of FIG. 4 is placed in the unlocked unbent position.

After the cannula 125 is properly placed so that it is adjacent to the target tissue, the shaft 155 is distally advanced to deploy the electrode array 175 radially outward from the distal end 145 of the cannula 125. This is accomplished using the actuator 250. For example, if the actuator 250 is a switch 250, as in the preferred embodiment, the switch 250 is pushed distally into the down position, as illustrated in FIG. 13, which pushes the cable 270, which in turn pushes the shaft 155, which thus deploys the electrode array 175. The shaft 155 is advanced sufficiently, so that the electrode array 175 fully everts in order to substantially penetrate the entire treatment region. If the probe assembly 115 has an optional core member (not shown in any of the accompanying drawings) previously mentioned, then the sharpened end of the core member facilitates introduction of the electrode array 175 into the treatment region.

Figure 14:
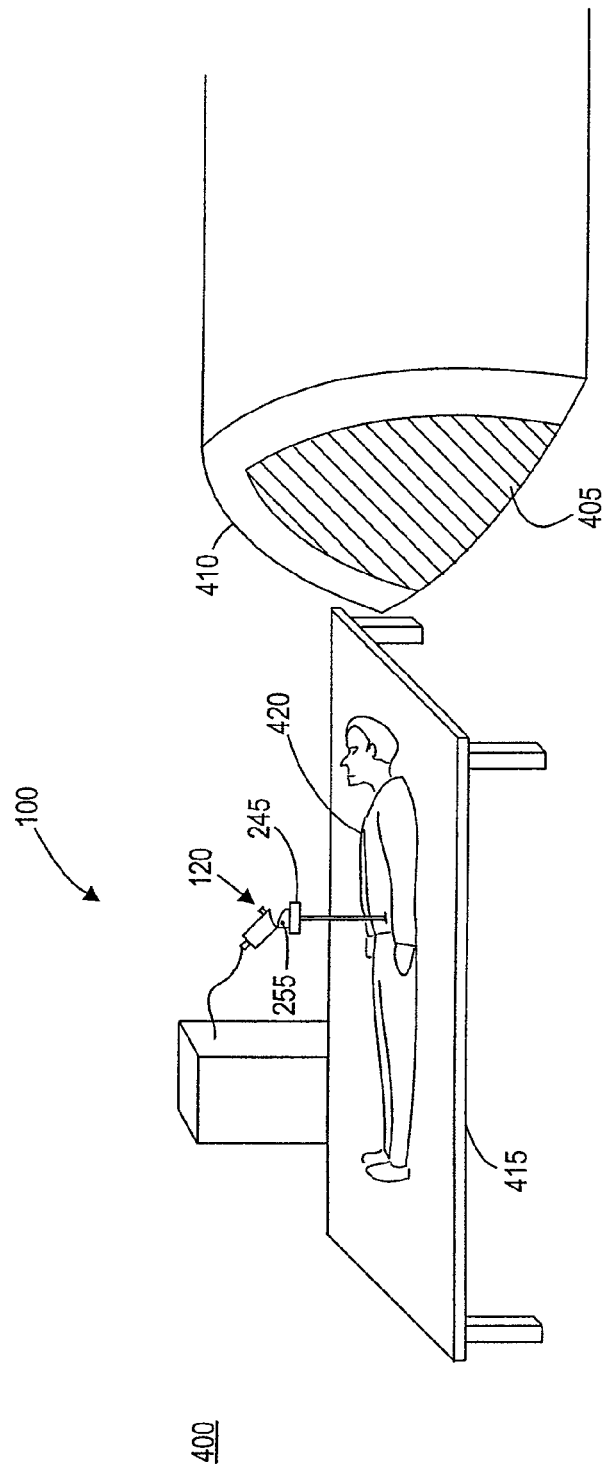
FIG. 14 is a perspective view of the patient, wherein the probe handle of FIG. 4 is placed in the unlocked bent position.

After the electrode array 175 is deployed within the target tissue, the handle assembly 120 is bent to reduce the overall probe assembly 115 height, as illustrated in FIG. 14. Specifically, the collar 245 is slid distally into the down position, exposing the hinge 255, and the handle assembly 120 is then bent at the hinge 255. In the alternate method—which uses the tissue ablation system that has a flexible handle 305—the operation 400 proceeds as described above, except that instead of sliding the collar 245 distally to expose the hinge 255 and then bending the handle assembly 120 at the hinge 255, the rigid sleeve 310 is removed and the handle 305 is flexed to reduce the overall height.

Figure 15:
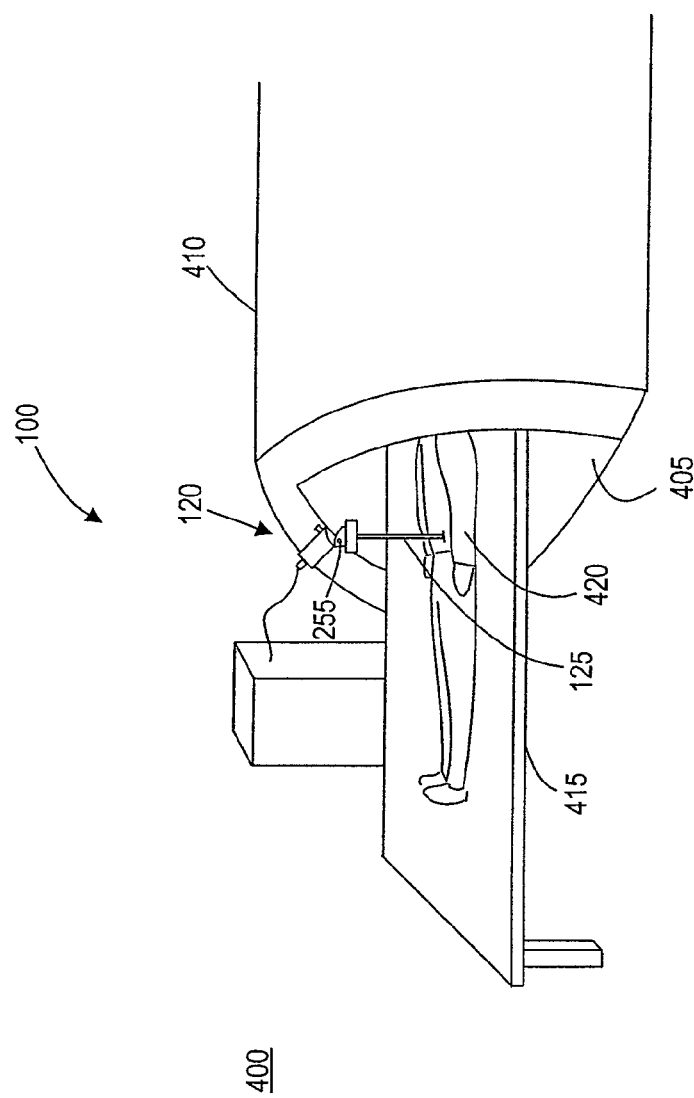
FIG. 15 is a perspective view of the patient, wherein the patient is placed into the imaging chamber, along with the probe assembly of FIG. 2, and the medical procedure is performed on the patient using the tissue ablation system of FIG. 1.

In any event, the table 415 with the patient 420 lying on it, is then slid into the confined space 405 of the imaging chamber 410, as shown in FIG. 15.

Although in the preferred method, the cannula 125 is inserted into the patient 420 and the handle assembly 120 is bent prior to placing the patient 420 and the medical probe assembly 115 into the confined space 405, as illustrated in FIGS. 12-15, the cannula 125 can be inserted into the patient 420 and the handle assembly 120 can be bent after placement of the patient 420 and the medical probe assembly 115 into the confined space 405.

Once the patient 420 is properly positioned within the imaging chamber 410, the tissue ablation system 100 is operated to perform the medical procedure, and specifically to ablate the target tissue within the patient 420. If the imaging device 410 is a computerized axial tomography chamber, the method can further comprise observing the medical procedure using computerized axial tomography. Likewise, if the imaging device 410 is a magnetic resonance chamber, the method can further comprise observing the medical procedure using magnetic resonance imaging.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A medical probe assembly for ablating tissue, comprising:
    a cannula having a proximal end and a distal end and a central lumen;
    an inner probe slideably disposed in the central lumen of the cannula, the inner probe comprising one or more ablative elements mounted thereon;
    a handle assembly mounted on the proximal end of the cannula, the handle assembly comprising first and second handle pieces arranged to form a single contiguous handle, and a hinge coupling the first and second handle pieces; and
    a slideable collar disposed on the handle assembly and configured for selectively covering and uncovering the hinge.

2. The medical probe assembly of claim 1, wherein the handle assembly is configured to be selectively placed in a locked position so that the handle assembly is substantially rigid, and an unlocked position so that the first and second handle pieces can rotate relative to each other.

3. The medical probe assembly of claim 1, wherein the single handle is generally cylindrical.

4. The medical probe assembly of claim 1, wherein the one or more ablative elements comprises one or more ablation electrodes.

5. The medical probe assembly of claim 4, wherein the handle assembly comprises a radio frequency connector, and one or more radio frequency wires electrically coupled between the radio frequency connector and the one or more electrodes.

6. The medical probe assembly of claim 5, wherein the radio frequency wires have slack.

7. The medical probe assembly of claim 5, further comprising a connector piece electrically coupled between the radio frequency connector and the radio frequency wires, the connector piece being slideably disposed inside of the radio frequency connector in an interference arrangement, while remaining in conductive contact with the radio frequency connector.

8. The medical probe assembly of claim 1, wherein the handle assembly comprises a slideable switch coupled to the inner probe for selectively deploying and retracting the one or more ablative elements.

9. The medical probe assembly of claim 8, further comprising a push-pull rod coupled between the slideable switch and the inner probe.

10. The medical probe assembly of claim 1, wherein the cannula is rigid, semi-rigid, or flexible.

11. The medical probe assembly of claim 1, wherein the single handle extends along a straight longitudinal axis.

12. A medical probe assembly, comprising:
    an elongated probe having a proximal end and a distal end;
    an operative element mounted on the distal end of the probe;
    a handle assembly mounted on the proximal end of the probe, the handle assembly comprising proximal and distal handle pieces arranged to form a single contiguous handle, a hinge coupling the proximal and distal handle pieces, and an actuator disposed in the proximal handle piece that can be manually manipulated to deploy the operative element; and
    a slideable collar disposed on the handle assembly and configured for selectively covering and uncovering the hinge.

13. The medical probe assembly of claim 12, wherein the handle assembly is configured to be selectively placed in a locked position so that the handle assembly is substantially rigid, and an unlocked position so that the proximal and distal handle pieces can rotate relative to each other.

14. The medical probe assembly of claim 12, wherein the single handle is generally cylindrical.

15. The medical probe assembly of claim 12, wherein the actuator can be manipulated to selectively deploy and retract the operative element.

16. The medical probe assembly of claim 12, wherein the actuator comprises a slideable switch coupled to a shaft carrying the operative element.

17. The medical probe assembly of claim 16, further comprising a push-pull rod coupled between the slideable switch and the shaft.

18. The medical probe assembly of claim 12, wherein the single handle extends along a straight longitudinal axis.

19. A medical probe assembly for ablating tissue, comprising:
    a cannula having a proximal end and a distal end and a central lumen;
    an inner probe slideably disposed in the central lumen of the cannula, the inner probe comprising one or more ablative elements mounted thereon;
    a bendable handle assembly mounted on the proximal end of the cannula;
    a moveable actuator disposed on the bendable handle assembly and operatively connected to the inner probe; and
    a rigid sleeve configured for selectively covering the bendable handle.

20. The medical probe assembly of claim 19, wherein the rigid sleeve comprises a slot dimensioned to accommodate the moveable actuator.

* * * * *